United States Patent [19]

Buehler et al.

[11] Patent Number: 5,426,163

[45] Date of Patent: Jun. 20, 1995

[54] REDISPERSIBLE POWDER COMPOSED OF N-VINYLPYRROLIDONE/VINYL ACETATE COPOLYMER THE PREPARATION AND USE THEREOF

[75] Inventors: Volker Buehler, Wachenheim; Sven Grabowski, Ludwigshafen; Axel Sanner, Frankenthal, all of Germany

[73] Assignee: BASF Aktiengesellschaft, Ludwigshafen, Germany

[21] Appl. No.: 314,911

[22] Filed: Sep. 19, 1994

Related U.S. Application Data

[63] Continuation of Ser. No. 983,410, Nov. 30, 1992, abandoned.

[30] Foreign Application Priority Data

Dec. 4, 1991 [DE] Germany .................. 41 39 963.3

[51] Int. Cl.[6] ........................................... C08F 2/08
[52] U.S. Cl. ............................. 526/207; 526/208; 526/210; 526/225; 526/264
[58] Field of Search ............... 526/207, 208, 210, 225

[56] References Cited

U.S. PATENT DOCUMENTS

| | | |
|---|---|---|
| 3,244,658 | 4/1966 | Grosser et al. . |
| 3,691,125 | 9/1972 | Barabas et al. . |
| 4,053,696 | 10/1977 | Herrle et al. .................. 526/65 |
| 4,167,439 | 9/1979 | Killam . |
| 4,182,851 | 1/1980 | Straub et al. . |
| 4,520,179 | 5/1985 | Barabas et al. .................. 526/212 |
| 4,906,701 | 3/1990 | Clark, Jr. .................. 526/207 |
| 5,077,040 | 12/1991 | Bergmann et al. .................. 424/70 |
| 5,122,582 | 6/1992 | Potthoff-Karl et al. . |

FOREIGN PATENT DOCUMENTS

| | | |
|---|---|---|
| 1544860 | 6/1969 | Germany . |
| 330141 | 7/1958 | Switzerland . |

*Primary Examiner*—Joseph L. Schofer
*Assistant Examiner*—Wu C. Cheng
*Attorney, Agent, or Firm*—Oblon, Spivak, McClelland, Maier, & Neustadt

[57] ABSTRACT

A process for preparing a free-flowing redispersible powder composed of a vinyl-pyrrolidone/vinyl acetate copolymer containing 15–40% by weight of vinylpyrrolidone units wherein the mixture of the monomers is copolymerized in organic solution, the resulting solution is, after addition of a surfactant, subjected to replacement of the solvent by water, and the resulting dispersion is spray- or freeze-dried, and the use of the redispersible powder for producing paints and coating compositions, glues and adhesives and, in particular, the matrix and/or coating of solid slow-release pharmaceutical forms and of hair-spray formulations are described.

5 Claims, No Drawings

REDISPERSIBLE POWDER COMPOSED OF N-VINYLPYRROLIDONE/VINYL ACETATE COPOLYMER THE PREPARATION AND USE THEREOF

This application is a Continuation of application Ser. No. 07/983,410, filed on Nov. 30, 1992, now abandoned.

The present invention relates to a process for preparing a free-flowing redispersible powder composed of a vinylpyrrrolidone (VP)/vinyl acetate (VAc) copolymer which is insoluble in water, to the powder as such and to its use, especially for the controlled release of active substances.

Vinylpyrrolidone/vinyl acetate solution polymers containing more than 50% by weight of vinyl acetate are insoluble in water and are employed for coatings etc., as solution in organic solvents. There are well known problems with the use of organic solvents: they are relatively costly, they can be recovered only with difficulty, and usually not at all, and thus pollute the environment, they are a fire and explosion hazard and are also not physiologically acceptable. The only alternative to these solution polymers would be the use of the corresponding dispersions. U.S. Pat. Nos. 3,244,658, 3,691,125 and 4,167,439 disclose that emulsion polymerizations with vinylpyrrolidone as comonomer (more than 10% by weight of the monomers) result in unstable and highly viscous dispersions which separate and, moreover, are poorly reproducible. Dispersions of this type can be obtained only by grafting vinyl acetate onto vinylpyrrolidone (PVP) introduced into the emulsion polymerization (U.S. Pat. No. 3,691,125). A secondary dispersion of such a copolymer of vinyl esters grafted onto vinylpyrrolidone is described in DE-A 15 44 860. However, the preparation process is very complicated: the graft copolymer is initially hydrolyzed, reacted with diketene, precipitated, washed with water and subsequently dissolved or emulsified in a water-miscible solvent, then dispersed in water and finally the solvent is removed by distillation.

Quite apart from the complexity of this process, the resulting graft copolymer is not comparable with a solution polymer of the same comonomers in the same ratio of amounts.

It is an object of the present invention to prepare in a straightforward manner a free-flowing redispersible powder of a vinylpyrrolidone/vinyl acetate solution polymer which is insoluble in water and which on stirring with cold water provides an aqueous formulation of the said polymer.

We have found that this object is achieved in that it is possible to prepare a stable secondary dispersion from organic solutions of vinylpyrrolidone/vinyl acetate solution copolymers which are insoluble in water, expediently directly from the polymerization solutions, by addition of one or more surfactants or emulsifiers, with or without protective colloids, and subsequent replacement of the solvent by water, from which dispersion free-flowing readily redispersible powders can be obtained by freeze- or spray-drying. The copolymer is prepared in a conventional manner from 15–40, preferably 20–35, % by weight of vinylpyrrolidone and 60–85, preferably 65–80, % by weight of vinyl acetate in an organic solvent (or mixture thereof) with a free radical initiator. It is advantageous to use solution polymers which already have a very low residual monomer content, as are described in U.S. Pat. No. 4,182,851. The Fikentscher K value (Cellulose-Chemie 13 (1932) 58–64 and 71–74) of the polymer should be in the range from 16 to 36, preferably 25 to 36, measured in 1% strength ethanolic solution at 25° C.

The surfactant is selected according to the requirements for subsequent use of the dispersion from the conventional anionic, cationic or non-ionic surfactants. The following surfactants have proven very useful, for example, for use of the dispersion in the pharmaceutical industry: sodium salt of ethylhexyl sulfosuccinate, arylsulfonates, approximately 9-fold ethoxylated stearic acid and sodium lauryl sulfate.

Suitable protective colloids are all compounds which can be used as such in emulsion polymerization, for example water-soluble cellulose derivatives, gelatin or PVP. They must form either true or colloidal solutions in water.

Replacement of the solvent can take place, for example, by steam distillation under atmospheric pressure or by stepwise addition of water and subsequent removal of the organic solvent under reduced pressure, and should result in removal of as much of the organic solvent as possible.

Examples of suitable organic solvents for the polymerization are aliphatic ketones with 3–5 carbon atoms, toluene and, in particular, lower aliphatic alcohols, especially ethanol or isopropanol, or mixtures thereof.

The secondary dispersion can be dried by freeze-or spray-drying, with or without the addition of spray auxiliaries and antiblocking agents. Spray-drying is carried out in a conventional manner in spray towers, it being possible to spray the dispersion in by means of atomizing disks or single- or multi-component nozzles. The dispersion is dried with hot gases, eg. with nitrogen or air.

The spray auxiliaries which are employed are one or more water-soluble substances with a second order phase transition point (glass transition temperature Tg) of at least 60° C., specifically in amounts of from 0 to 50% of the weight of the polymer. Particularly suitable spray auxiliaries have proven to be water-soluble polymers, especially those with high degrees of polymerization. Examples which may be mentioned are polyvinyl alcohols, ligninsulfonates, water-soluble condensates of naphthalenesulfonic acid and formaldehyde, polyacrylic acids and polyacrylamides.

To increase the storage stability of, for example, redispersible powders with a low glass transition temperature, in order to prevent caking and blocking, and thus improve the redispersibility, the resulting powder can be mixed with from 0 to 30% by weight, based on the total weight of polymeric components, of antiblocking agents. All the antiblocking agents customary for such purposes are suitable, for example colloidal silica, talc, clays and calcium carbonate.

Space- and weight-saving transport of the redispersible powder is possible until it is used to prepare the dispersion used as coating agent, and it can be stored as dry powder without the risk of loss of quality. The properties of the solution polymer are essentially retained in the dispersed state. Thus, the films obtained on drying the organic solution of the polymer are essentially equivalent to those obtained after drying the secondary dispersion as long as only small amounts of auxiliary were needed to prepare the secondary dispersion. Furthermore, the replacement of the solvent, which is equivalent to stripping the dispersion with steam, results in a reduction in unwanted volatile low molecular weight constituents. It is possible in this way, in particular, to decrease the residual vinyl acetate monomer content and reduce the odor compared with the solution polymer.

The redispersible powders obtainable by the process according to the invention can be redispersed simply by stirring with cold water, and the resulting dispersion has essentially the same properties as the secondary dispersion originally obtained on replacement of the solvent as long as there has been no addition of large amounts of auxiliary. They can be used advantageously for example, in the building sector, in the production of paints and coating agents and of glues and adhesives. They have proven particularly useful as binders and coating agents for slow-release pharmaceutical forms with pH-independent control of release of the active substance, and as film-formers for hair spray formulations.

Solid pharmaceutical forms with controlled release of the active substance by use of polymer are usually marketed as matrix tablets, film-coated tablets or coated pellets or granules with or without a hard gelatin capsule. The polymers normally used are cellulose derivatives, shellac or methacrylate copolymers (H. Sucker, P. Fuchs, P. Speiser, Pharmazeutische Technologie, G. Thieme-Verlag Stuttgart, 1978, 349–354). These polymers envelope the active substance, and it is liberated in gastric and/or intestinal fluid by slow diffusion through the polymer and/or erosion of the polymer as a function of the pH or independent thereof. One aim in this connection must be to achieve adequate release at the outset in order to reach the minimum concentration of active substance in the blood, and this must be followed by slower release of active substance.

The techniques of use of the powders and dispersions obtainable according to the invention are those customary in pharmaceutical technology:

matrix tablets or granules can be produced by traditional wet granulation of the active substance in a kneader/mixer or by fluidized bed granulation. This entails use of the aqueous dispersion of the powder obtainable according to the invention as binder suspension. Alternatively, the pharmaceutical substance can be mixed with the redispersible powder obtainable according to the invention, and this mixture can be granulated with a solvent, preferably water or alcohols, by the abovementioned methods. A combination of the two methods may be worthwhile in some cases. In some circumstances it is advisable to add a filler to the active substance (e.g. lactose, starch, calcium hydrogen phosphate) and/or an anti-stick agent (eg. talc). After the wet granules have been screened and dried they can be either packaged as such or packed into hard gelatin capsules or compressed to tablets after addition of further auxiliaries (eg. lubricants). Pellets can be produced by making a solution or fine dispersion of the active substance in the aqueous dispersion of the powder obtainable according to the invention. Particles of carrier material (eg. sugar beads) are then coated with this dispersion in a conventional manner, eg. in a fluidized bed, until the required amount of active substance has been applied. Another coating of the pellets with the dispersion of the powder obtainable according to the invention without active substance can be applied for additional control of release of active substance from the pellets.

Film-coated tablets according to the invention are produced by applying an aqueous dispersion (or else an organic, preferably alcoholic, solution) of the powder obtainable according to the invention together with the additives customary for tablet coatings (eg. pigments, lacquers, talc) to the cores which contain the active substance in a fluidized bed, coating pan, Accela-Cota or comparable apparatus.

This results in pH-independent control of release of active substance comparable with that with other slow-release film formers hitherto customary. It is possible by altering the ratio of amounts of vinylpyrrolidone and vinyl acetate to control the release profile of the active substance.

EXAMPLE 1

A copolymer of 30% by weight of vinylpyrrolidone and 70% by weight of vinyl acetate (prepared by solution polymerization in isopropanol, Fikentscher K value 28±3, measured on a 1% solution of the polymer in ethanol at 25° C.) as a 50% strength solution in isopropanol was mixed with 0.1% by weight (based on the polymer) of sodium lauryl sulfate and steam distilled, while stirring, until all the isopropanol had been replaced by water. The result was a wide dispersion whose solids content was adjusted to 30%. The viscosity of the dispersion was 159 mPas, and the residual vinylpyrrolidone and vinyl acetate monomer content was less than 2 ppm of the polymer. Further stabilization of this dispersion was achieved by adding about 1% by weight of 9-fold ethoxylated stearic acid.

The dispersion was adjusted to a solids content of about 20% and then freeze-dried, and the dried residue was ground to give a fine, free-flowing, non-blocking powder. There was no caking after storage at about 25° C. for several months.

EXAMPLE 2

A copolymer of 30% by weight of vinylpyrrolidone and 70% by weight of vinyl acetate (prepared by solution polymerization in ethanol, K value 32±4, measured as in Example 1), as a 50% strength solution in ethanol was mixed with 0.1% by weight, based on the polymer, of sodium lauryl sulfate and treated as in Example 1. The 30% strength dispersion had a viscosity of 4200 mPas. It was diluted to twice the volume with water and then spray-dried. The inlet temperature was about 120° C., and the outlet temperature was about 80° C. The result was a free-flowing, non-blocking, fine product composed of agglomerated particles of relatively uniform structure. There was no caking after storage at about 25° C. for several months.

EXAMPLE 3

A copolymer of 20% by weight of vinylpyrrolidone and 80% by weight of vinyl acetate (prepared by solution polymerization in isopropanol, K value 19±3, measured as in Example 1), as a 50% strength solution in isopropanol was mixed with 1.6% by weight, based on the polymer, of sodium lauryl sulfate and steam distilled as in Example 1. The dispersion was adjusted to 25% by weight and then stabilized by addition of 1% by weight of the sodium salt of ethylhexyl sulfosuccinate. Dilution with water to a solids content of about 15% was followed by spray-drying. The inlet temperature was about 105° C. and the outlet temperature was about 70° C. The resulting powder had similar properties to that of Example 2.

The powders obtained as in Examples 1 to 3 were easily dispersible by stirring in cold water. The resulting dispersions (whose solids concentration could be adjusted virtually as required) gave on drying uniform films whose transparency and brittleness were virtually the same as those from an organic solution of the solution polymer. The minimum film-forming temperature (measured by the DIN 53 787 method) of these dispersions was 14°–17° C.

EXAMPLE 4

An aqueous dispersion of the powder obtained as in Example 1 was used to produce matrix tablets of the following formulation:

1. Composition

| I | Theophylline | 125 g |
|---|---|---|
|  | Calcium hydrogen phosphate | 75 g |
| II | Vinylpyrrolidone/vinyl acetate copolymer 30% dispersion | 33 g |
|  | Water | 27 g |
| III | Magnesium stearate | 1 g |

Mixture I was granulated with dispersion II in a fluidized bed granulator and was screened, dried, mixed with III and tableted under low compressive force in a rotary tableting machine.

2. Physical properties of the tablets

| Weight | 213 mg |
|---|---|
| Diameter | 8 mm |
| Hardness (Schleuniger method) | 186 N |
| Friability (Roche Friabilator) | 0.2% |

3. Theophylline release

The release of theophylline was determined by the paddle method of US Pharmacopeia XXII at 50 revolutions per minute. A matrix tablet produced in a similar manner with a commercial ethyl acrylate/methyl methacrylate copolymer in place of the vinylpyrrolidone/vinyl acetate copolymer according to the invention was used for comparison. The release profiles were very similar to one another but the matrix of Example 1 proved to be more favorable because the release was somewhat higher at the start and somewhat lower later on than with the comparison tablets.

EXAMPLE 5

The redispersible powder according to the invention from Example 1 was used to prepare a dispersion with a solids content of 10% by weight in distilled water. This dispersion was very suitable as a pump spray for hair setting. The film was clear and even without the addition of a flow controller displayed a pleasant gloss. For practical applications merely perfume oils were added.

We claim:

1. A method of preparing a free-flowing redispersible powder comprising (a) a vinylpyrrolidone/vinyl acetate copolymer containing 15–40% by weight vinylpyrrolidone monomer units, and (b) a surfactant or emulsifier, comprising:
   (1) polymerizing vinylpyrrolidone and vinyl acetate in an organic solution to obtain a solution of said copolymer;
   (2) adding a surfactant or emulsifier to said solution;
   (3) replacing said organic solvent with water to form an aqueous dispersion of said copolymer and surfactant; and
   (4) spray drying or freeze drying said dispersion to form said free-flowing redispersible powder.

2. The method of claim 1, wherein 0.1–1.6 wt. % of said surfactant based on said copolymer is added to said solution.

3. The method of claim 1, wherein about 1 wt. % of a protective colloid is added to said solution.

4. The method of claim 1, wherein a spray auxiliary is added to said aqueous dispersion in an amount up to about 50% by weight of said copolymer.

5. The method of claim 1, further comprising (5) adding an anti-blocking agent to said redispersible powder in an amount up to 30% by weight of the polymeric components in said redispersible powder.

* * * * *